Figures 1, 2:
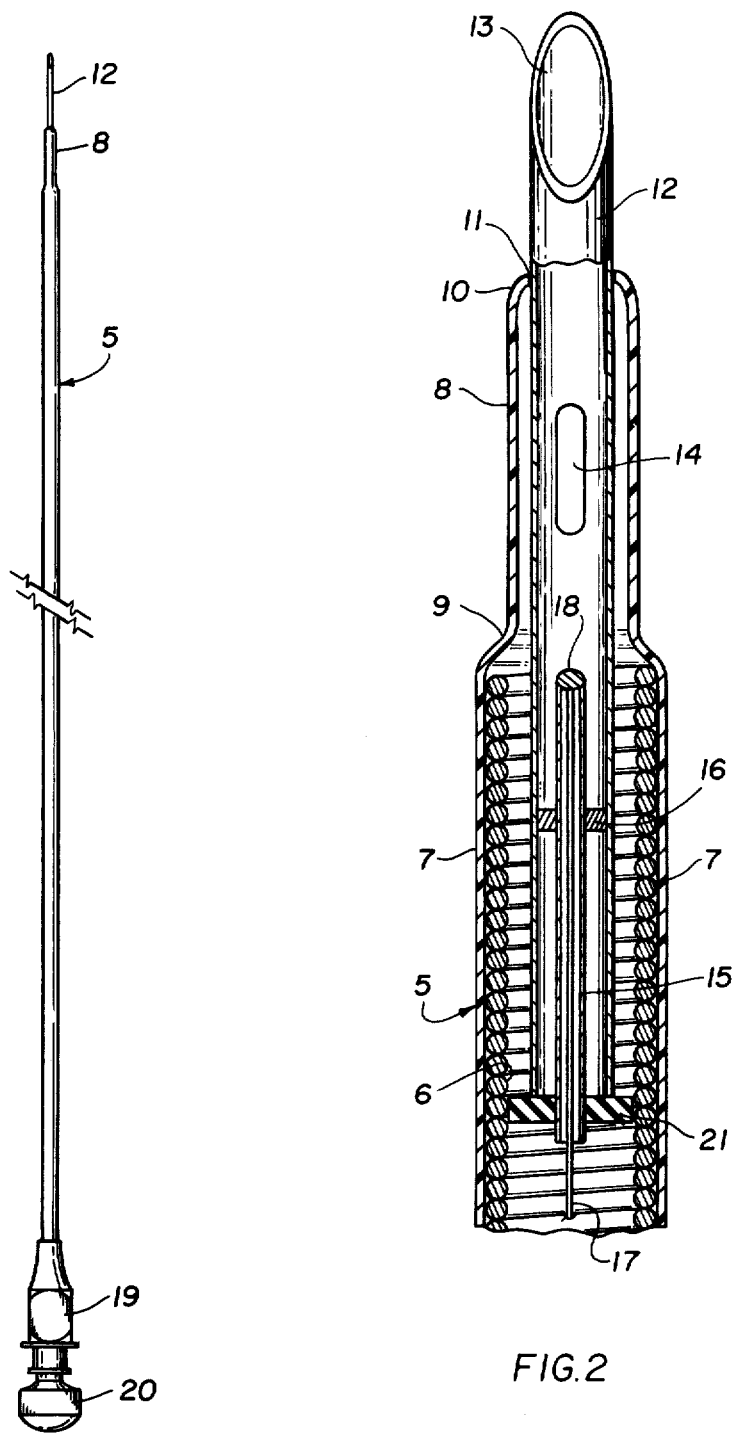

United States Patent [19]

Kline

[11] 4,052,989
[45] Oct. 11, 1977

[54] NEEDLE CATHETER

[75] Inventor: William Mathes Kline, Gloversville, N.Y.

[73] Assignee: Medical Evaluation Devices and Instruments Corporation, Gloversville, N.Y.

[21] Appl. No.: 627,066

[22] Filed: Oct. 30, 1975

[51] Int. Cl.$^2$ .................................... A61M 25/00
[52] U.S. Cl. .................... 128/349 R; 128/2 M; 128/DIG. 16
[58] Field of Search ............ 128/348, 349 R, 349 B, 128/349 BV, 350 R, 350 V, 351, DIG. 9, DIG. 16, 2 M, 221

[56] References Cited

U.S. PATENT DOCUMENTS

| | | | |
|---|---|---|---|
| 1,752,384 | 4/1930 | Jamison | 128/221 X |
| 1,881,415 | 10/1932 | Tingleff | 128/221 X |
| 2,748,769 | 6/1956 | Huber | 128/221 |
| 2,770,236 | 11/1956 | Utlex et al. | 128/221 |
| 3,097,646 | 7/1963 | Scislowicz | 128/DIG. 16 |
| 3,515,137 | 6/1970 | Santomieri | 128/348 X |
| 3,612,050 | 10/1971 | Sheridan | 128/348 X |
| 3,739,778 | 6/1973 | Monestere, Jr. et al. | 128/DIG. 16 |
| 3,757,768 | 9/1973 | Kline | 128/DIG. 9 |
| 3,769,975 | 11/1973 | Nimoy et al. | 128/348 X |
| 3,809,081 | 5/1974 | Loveless | 128/348 X |
| 3,841,307 | 10/1974 | Friedell | 128/221 |
| 3,875,938 | 4/1975 | Mellor | 128/DIG. 16 |
| 3,894,540 | 7/1975 | Bonner, Jr. | 128/350 R X |

OTHER PUBLICATIONS

Catalog of A. S. Aloe Co., 12/20/60.

Primary Examiner—Louis G. Mancene
Assistant Examiner—Paul J. Hirsch
Attorney, Agent, or Firm—Thomas E. Tate

[57] ABSTRACT

The disclosure is that of an invention directed to a catheter that includes an internal, distally projecting, proximally removable, puncture needle, thus enabling the catheter to be introduced into a vessel of an animate being without first having to use a sharpened cannula or split needle. A sight zone adjacent the distal end is provided to visually observe blood flow as an indication of proper and accurate insertion.

2 Claims, 2 Drawing Figures

U.S. Patent    Oct. 11, 1977    4,052,989

NEEDLE CATHETER

THE INVENTION

This invention relates generally to new and useful improvements in those types of catheters that are used for catheterization of the heart and/or internal vessels of the body during certain diagonostic testing and treating procedures and particularly seeks to provide a novel catheter for such purposes that can be directly percutaneously inserted into the vessel.

Heretofore, in order to introduce a catheter into the lumen of a vessel it has been necessary to first percutaneously insert a sharpened cannula or hollow split needle into the vessel and then insert the catheter through the cannula, after which the cannula is removed. Such a procedure obviously requires two steps to effect insertion of the catheter and also obviously requires the use of a cannula or split needle that has an outside diameter substantially greater than that of the catheter, thus abnormally dilating the vessel at the zone insertion.

However, a catheter constructed in accordance with this invention overcomes such problems by being directly insertable into the vessel without first requiring the use of sharpened cannula or split needle and without causing any abnormal dilation of the vessel in the zone of initial insertion.

However, a catheter constructed in accordance with this invention overcomes such problems by being directly insertable into the vessel without first requiring the use of a sharpened cannula or split needle and without causing any abnormal dilation of the vessel in the zone of initial insertion.

Therefore, an object of this invention is to provide a catheter that can be directly percutaneously inserted into a vessel of an animate being.

Another object of this invention is to provide a catheter of the character stated in which a retraction wire extends through the lumen thereof and has one end secured to the insertion needle and its other end extending proximally beyond the proximal end of the catheter for connection to a retracting knob or handle.

A further object of this invention is to provide a catheter of the character stated in which the distal end portion thereof is transparent in order to provide a sight zone and in which the insertion needle is provided with a radial aperture in register with the sight zone to permit blood to flow thereinto and provide visible indication that the needle has been accurately and properly inserted into the lumen of the vessel.

A further object of this invention is to provide a catheter of the character stated that is simple in design, rugged in construction and economical to manufacture.

With these and other objects, the nature of which will become apparent, the invention will be more fully understood by reference to the drawings, the accompanying detailed description and the appended claims.

In the drawings:

FIG. 1 is a side elevation of an assembled needle catheter constructed in accordance with this invention; and FIG. 2 is an enlarged detail longitudinal section of the distal end portion thereof.

Before referring to the drawings in detail it should be understood that the novel self-piercing features of the catheters constructed in accordance with this invention are equally applicable to tubular catheter bodies formed from extruded or circularly braided materials, although preferebly the body construction should be of a plastic sheathed, close wound, stainless steel spring such as that disclosed in U.S. Pat. No. 3,757,768, granted Sept. 11, 1973; and the remainder of this description will be directed to that preferred construction because it provides the safety feature at the distal end of the body spring of having the outer sheathing necked down to prevent axial elongation of the body spring and because such a construction is stronger and provides a smaller outside diameter for each desired lumen capacity than do the other body constructions.

Referring to the drawings in detail, a preferred form of the invention, as illustrated, is embodied in a flexible catheter generally indicated 5 that may be made in any required length, for example, from 20 cm. to 150 cm. or more, and of a size ranging from a No. 2 to a No. 15 French.

The catheter 5 includes an inner wall portion 6 defined by a continuous helical spring wound with the helices thereof in contact with each other and formed from stainless steel spring wire, and an outer sheathing 7 formed from a tube of smooth, inert transparent, flexible plastic material, such as a halogenated hydrocarbon or the equivalent thereof, that is heatshrunk over the spring 6 in such a manner that the outer surface of the plastic tube remains smooth and its inner surface is forced into the spiral grooves on the outer surface of the spring, thus effecting a firm bond between the sheathing tube and the spring.

The distal end of the tubular sheathing 7 extends distally beyond the distal end of the spring 6 to define a distally extending transparent straight tip 8 that is necked down as at 9, as the result of the initial heatshrinking or subsequent heat-drawing to lock the distal end of the spring against axial elongation and to provide a smaller outside diameter for the tip 8 which enhances its advance into and along a vessel.

The distal end of the tip 8 is heat-drawn or otherwise formed into a taper 10 having a lip 11 that is adapted to fit closely around an internal insertion or puncture needle, as now will be more fully described.

A hollow insertion or puncture needle 12 is frictionally and slidably retained within the distal end of the catheter 5 by the lip 11 and is provided at its distal end with a sharpened point 13. An aperture 14 is formed in an intermediate wall portion of the needle and is disposed in registry with the middle portion of the transparent tip 8 to permit blood to flow into the void between the needle and the tip when the needle initially is inserted into a vessel, thus enabling the tip 8 to serve as a sight tube and provide a visible indication of the correctness of entry of the needle into the vessel. Once that has been determined, the catheter and needle are bodily advanced further until at least a portion of the tip 8 has entered the vessel, after which the needle is proximally removed from the catheter and the catheter is then fully advanced into the vessel in the usual manner under fluoroscopic observation.

The means for proximally removing the needle include a metal sleeve 15, preferably formed from small diameter needle tubing, that is inserted within the proximal end portion of the needle 12, and secured therein as by an annular seal or weld as indicted at 16, which also serves as a dam to prevent blood flow therebeyond in a proximal direction. A retraction wire 17 extends through the lumen of the catheter and has its distal end threaded through the sleeve 15 and secured to the distal end thereof as by a ball weld 18 or other suitable means.

The proximal end of the catheter 5 is provided with the usual female Luer fitting 19 (see FIG. 1) which initially receives a male Luer fitting 20 that is attached to the proximal end of the retraction wire 17, so that proximal movement of the fitting 20 relative to the catheter will effect a complete withdrawal of the needle 12 through the lumen of the catheter by the retraction wire.

In assembling the needle catheter, the distal end of the retraction wire 17 is first attached to the needle sleeve 15 as described above and then the proximal portion of the retraction wire is threaded through the lumen of the catheter 5 from the distal end to the proximal end thereof and the proximal portion of the needle 12 is inserted through the distal lip 11 of the tip 8 until the aperture 14 is in register with the mid-portion of the tip and the sharpened point 13 extends distally the desired distance therebeyond. At this stage the proximal end of the retraction wire 17 projects proximally beyond the proximal end of the catheter for attachment to the male Luer fitting 20 which is then seated in the fitting 19, thus imparting a slack condition to the retraction wire so that normal handling and flexing of the assembled unit as an incident to its use will not cause an inadvertant partial retraction of the needle.

For some sizes of the catheters where the inside diameter of the spring 6 may be relatively substantially greater than the outside diameter of the needle 12, it may be desirable to provide a centering sliding support or guide adjacent the proximal end of the needle. For this purpose an elastomeric washer 21, having a diameter to fit closely but slidingly within the spring 6, is fitted over the proximal end of the sleeve 15 in abutting relation to the proximal end of the needle 12, and can slide relative to the spring when the needle is proximally retracted. Because the centering washer 21 provides the additional benefit of preventing blood flow around the exterior of the needle 12 proximally beyond its proximal end until the needle is fully retracted, it may be desirable to include the centering washer in all sizes of catheters.

It is of course to be understood that variations in arrangements and proportions of parts may be made within the scope of the appended claims.

I claim:

1. In a needle catheter wherein is provided a lumen-defining flexible tubular body having proximal and distal ends, a relatively short puncture needle frictionally retained within the distal end portion of said tubular body and means for proximally retracting said puncture needle through the lumen of said tubular body; the improvement in which said tubular body is formed with a lumen having a diameter greater than the outside diameter of said puncture needle and in which at least the distal end portion of said tubular body is transparent whereby to provide a sight zone surrounding the associated portion of said puncture needle, said puncture needle being hollow and being provided with a radial aperture located in registry with a portion of said sight zone for passage of fluid thereinto when said puncture needle is inserted into a fluid-containing vessel, said tubular body comprising an inner wall formed from a continuous helical spring with the helices thereof in contact with each other and an outer sheathing of smooth inert plastic material firmly bonded thereto, said outer sheathing extending distally beyond the distal end of said spring to define a hollow tip having proximal and distal ends, the proximal end of said hollow tip being configured to restrain said spring against axial elongation in a distal direction, the distal end of said hollow tip being configured to define an annular lip of reduced diameter for frictional engagement with and sliding retention of said puncture needle; and in which means slidably retained within said tubular body in association within the proximal end of said puncture needle are provided for preventing fluid flow around the exterior of said needle proximally beyond the proximal end thereof.

2. In a needle catheter wherein is provided a lumendefining flexible tubular body having proximal and distal ends, a relatively short puncture needle frictionally retained within the distal end portion of said tubular body and means for proximally retracting said puncture needle through the lumen of said tubular body; the improvement in which said tubular body is formed with a lumen having a diameter greater than the outside diameter of said puncture needle and in which at least the distal end portion of said tubular body is transparent whereby to provide a sight zone surrounding the associated portion of said puncture needle, said puncture needle being hollow and being provided with a radial aperture located in registry with a portion of said sight zone for passsage of fluid thereinto when said puncture needle is inserted into a fluid-containing vessel, said tubular body comprising an inner wall formed from a continuous helical spring with the helices thereof in contact with each other and an outer sheathing of smooth inert plastic material firmly bonded thereto, said outer sheathing extending distally beyond the distal end of said spring to define a hollow tip having proximal and distal ends, the proximal end of said hollow tip being configured to restrain said spring against axial elongation in a distal direction, the distal end of said hollow tip being configured to define an annular lip of reduced diameter for frictional engagement with the sliding retention of said puncture needle; and in which means are provided for preventing fluid flow in a proximal direction both through and around the proximal end of said puncture needle.

* * * * *